US006706721B1

(12) United States Patent
Allen et al.

(10) Patent No.: US 6,706,721 B1
(45) Date of Patent: Mar. 16, 2004

(54) N-(3-ETHYNYLPHENYLAMINO)-6,7-BIS(2-METHOXYETHOXY)-4-QUINAZOLINAMINE MESYLATE ANHYDRATE AND MONOHYDRATE

(75) Inventors: Douglas John Meldrum Allen, New London, CT (US); Timothy Norris, Gales Ferry, CT (US); Jeffrey William Raggon, Teecomwas, CT (US); Dinos Paul Santafianos, Manchester, CT (US); Ravi Mysore Shanker, Groton, CT (US)

(73) Assignee: OSI Pharmaceuticals, Inc., Melville, NY (US)

( * ) Notice: Subject to any disclaimer, the term of this patent is extended or adjusted under 35 U.S.C. 154(b) by 0 days.

(21) Appl. No.: 09/355,534

(22) PCT Filed: Apr. 8, 1999

(86) PCT No.: PCT/IB99/00612

§ 371 (c)(1),
(2), (4) Date: Jul. 29, 1999

(87) PCT Pub. No.: WO99/55683

PCT Pub. Date: Nov. 4, 1999

Related U.S. Application Data
(60) Provisional application No. 60/083,441, filed on Apr. 29, 1998.

(51) Int. Cl.$^7$ ............... C07D 239/94; A61K 31/517
(52) U.S. Cl. .................... 514/266.3; 544/293
(58) Field of Search ................. 544/283, 293; 514/259, 266.3

(56) References Cited

U.S. PATENT DOCUMENTS

| | | | |
|---|---|---|---|
| 5,580,870 A | 12/1996 | Barker et al. | |
| 5,616,582 A | 4/1997 | Barker | |
| 5,639,881 A | 6/1997 | Skibo et al. | |
| 5,654,307 A | 8/1997 | Bridges et al. | |
| 5,686,458 A | 11/1997 | Lee et al. | |
| 5,707,992 A | 1/1998 | Webber et al. | |
| 5,710,145 A | 1/1998 | Engel et al. | |
| 5,747,498 A | * 5/1998 | Schnur et al. | ............... 514/259 |
| 5,770,195 A | 6/1998 | Hudziak et al. | |

FOREIGN PATENT DOCUMENTS

| | | |
|---|---|---|
| JP | 7309873 | 11/1992 |
| JP | 8099962 | 7/1993 |
| JP | 7126255 | 9/1994 |
| JP | 9165385 | 8/1995 |
| JP | 7188244 | 9/1995 |
| JP | 9221478 | 2/1997 |
| NZ | 0245662 | 1/1993 |
| RU | 2127263 | 1/1993 |
| WO | WO9220642 | 11/1992 |
| WO | WO9503283 | 2/1995 |
| WO | WO9515758 | 6/1995 |
| WO | WO9609294 | 3/1996 |
| WO | WO9615118 | 5/1996 |
| WO | WO9628430 | 9/1996 |
| WO | WO9640210 | 12/1996 |

OTHER PUBLICATIONS

Moyer et al., Cancer Research, 57, 4838–4848, 1997.*

Hussain, M., et al., "Parenteral Formulationof the Kappa Agonist Analgesic, DuP 747, via Micellar Solubilization," *Pharmaceutical Research* 1992, vol. 9, No. 6, p.p. 750–752 (Exhibit 79).

Moyer, J., et al., "Induction of Apoptosis and Cell Cycle Arrest by CP-357,774, an Inhibitor of Epidermal Growth Factor Receptor Tyrosine Kinase," *Cancer Research* 1997, vol. 57, p.p. 4838–4848 (Exhibit 80).

Norris, T., et al., "Discovery of a New Stable Polymorph of 4–(3–ethynylphenylamino)–6, 7–bis(2–methoxy–ethoxy)quinazolinium Methanesulfonate Using Near–Infrared Spectroscopy to Monitor Form Change Kinetics," *J. Chem. Soc., Perkin Trans.* 2000, vol. 2, p.p. 1233–1236 (Exhibit 81).

Onopchenko, et al., "Selective Catalytic Hydrogenation of Aromatic Nitro Groups in the Presence of Acetylenes. Synthesis of (3–Aminophenyl)acetylene via Hydrogenationof Dimethylcarbinol Substituted (3–Nitrophenyl) acetylene over Heterogeneous Metallic Ruthenium Catllyst," *Journal of Organic Chemistry* 1979, vol. 44, No. 8, p.p. 1233–1236 (Exhibit 82).

Pollack, V., et al., "Inhibition of Epidermal Growth Factor Recepto–Associated Tyrosine Phsophorylation in Human Carcinomas with CP–358,774: Dynamics of Recpetor Inhibiton In Situ and Antitumor Effects i Athymic Mice," *Journal of Pharmacology and Experimetnal Therapeutics*, 1999, vol. 291, No. 2, p.p. 739–748 (Exhibit 83).

Rosenberg, S., et al., "Studies Directed toward the Design of Orally Active Renin Inhibotrs. 2. Developmetn of the Efficacious, Bioavailable Renin Inhibitor (2S)–2–Benzyl–3–[[[(1–methylpiperazine–4–yl)sulfonyl]propi-nonyl]–3–thiazol–4–yl–L–alanine Amide of (2S, 3R, 4S)–2–Amino–1–cyclohexyl–3, 4–dihydroxy–6–methylheptane (A–72517)," *J. Med. Chem.* 1993, vol. 36, p.p. 460–467 (Exhibit 84).

Moyer et al., Cancer Research, 57, 4838–4848, 1997.*

* cited by examiner

*Primary Examiner*—John M. Ford
(74) *Attorney, Agent, or Firm*—John P. White; Cooper & Dunham LLP

(57) ABSTRACT

The present invention relates to the anhydrous and hydrate forms of N-(3-ethynylphenyl)-6,7-bis(2-methoxyethoxy)-4-quinazolinamine mesylate. The invention also relates to pharmaceutical compositions containing N-(3-ethynylphenyl)-6,7-bis(2-methoxyethoxy)-4-quinazolinamine mesylate and to methods of treating hyperproliferative disorders, such as cancer, by administering N-(3-ethynylphenyl)-6,7-bis(2-methoxyethoxy)-4-quinazolinamine mesylate.

12 Claims, No Drawings

US 6,706,721 B1

N-(3-ETHYNYLPHENYLAMINO)-6,7-BIS(2-METHOXYETHOXY)-4-QUINAZOLINAMINE MESYLATE ANHYDRATE AND MONOHYDRATE

This application is a national stage under 35 U.S.C. §371 of PCT International Application No. PCT/IB 99/00612, filed Apr. 8, 1999, which claims the benefit of U.S. Provisional Application No. 06/083,441, filed Apr. 29, 1998.

BACKGROUND OF THE INVENTION

The present invention relates to novel N-(3-ethynylphenyl)-6,7-bis(2-methoxyethoxy)-4-quinazolinamine mesylate anhydrous and hydrate forms. These compounds are useful in the treatment of hyperproliferative disorders, such as cancers, in mammals.

U.S. Pat. No. 5,747,498, issued May 5, 1998, which is incorporated herein by reference in its entirety, refers to [6,7-bis(2-methoxyethoxy)-quinazolin-4-yl]-(3-ethynylphenyl)amine hydrochloride which, the patent application discloses, is an inhibitor of the erbB family of oncogenic and protooncogenic protein tyrosine kinases, such as epidermal growth factor receptor (EGFR), and is therefore useful for the treatment of proliferative disorders, such as cancers, in humans. The mesylate compounds of the present invention are similarly useful for the treatment of proliferative disorders, but they also possess certain advantages over the foregoing hydrochloride compound. One advantage is that the mesylate compounds of the present invention are more soluble in aqueous compositions than the above hydrochloride compound, and thus the mesylate compounds of the present invention are easily delivered according to parenteral methods of administration.

SUMMARY OF THE INVENTION

The present invention relates to the anhydrous and hydrate forms of N-(3-ethynylphenyl)-6,7-bis(2-methoxyethoxy)-4-quinazolinamine mesylate.

A specific embodiment of the present invention comprises the anhydrous form of N-(3-ethynylphenyl)-6,7-bis(2-methoxyethoxy)-4-quinazolinamine mesylate. In particular, the anhydrous form includes polymorphs A, B, and C, having X-ray powder diffraction patterns as described below.

Another specific embodiment of the present invention comprises N-(3-ethynylphenyl)-6,7-bis(2-methoxyethoxy)-4-quinazolinamine mesylate monohydrate.

The invention also relates to a pharmaceutical composition for the treatment of a hyperproliferative disorder in a mammal which comprises a therapeutically effective amount of N-(3-ethynylphenyl)-6,7-bis(2-methoxyethoxy)-4-quinazolinamine mesylate, and a pharmaceutically acceptable carrier. In one embodiment, said pharmaceutical composition is for the treatment of cancer such as brain, lung, squamous cell, bladder, gastric, pancreatic, breast, head, neck, renal (such as kidney), ovarian, prostate, colorectal, oesophageal, gynecological or thyroid cancer. In another embodiment, said pharmaceutical composition is for the treatment of a non-cancerous hyperproliferative disorder such as benign hyperplasia of the skin (e.g., psoriasis) or prostate (e.g., benign prostatic hypertropy (BPH)).

The invention also relates to a pharmaceutical composition for the treatment of pancreatitis or kidney disease (including proliferative glomerulonephritis and diabetes-induced renal disease) in a mammal which comprises a therapeutically effective amount of N-(3-ethynylphenyl)-6,7-bis(2-methoxyethoxy)-4-quinazolinamine mesylate and a pharmaceutically acceptable carrier.

The invention also relates to a pharmaceutical composition for the prevention of blastocyte implantabon in a mammal which comprises a therapeutically effective amount of N-(3-ethynylphenyl)-6,7-bis(2-methoxyethoxy)-4-quinazolinamine mesylate and a pharmaceutically acceptable carrier.

The invention also relates to a pharmaceutical composition for treating a disease related to vasculogenesis or angiogenesis in a mammal which comprises a therapeutically effective amount of N-(3-ethynylphenyl)-6,7-bis(2-methoxyethoxy)-4-quinazolinamine mesylate and a pharmaceutically acceptable carrier. In one embodiment, said pharmaceutical composition is for treating a disease selected from the group consisting of tumor angiogenesis, chronic inflammatory disease such as rheumatoid arthritis, atherosclerosis, skin diseases such as psoriasis, excema, and scieroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a method of treating a hyperproliferative disorder in a mammal which comprises administering to said mammal a therapeutically effective amount of N-(3-ethynylphenyl)-6,7-bis(2-methoxyethoxy)-4-quinazolinamine mesylate. In one embodiment, said method relates to the treatment of cancer such as brain, squamous cell, bladder, gastric, pancreatic, breast, head, neck, oesophageal, prostate, colorectal, lung, renal (such as kidney), ovarian, gynecological or thyroid cancer. In another embodiment, said method relates to the treatment of a non-cancerous hyperproliferative disorder such as benign hyperplasia of the skin (e.g., psoriasis) or prostate (e.g., benign prostatic hypertropy (BPH)).

The invention also relates to a method for the treatment of a hyperproliferaive disorder in a mammal which comprises administering to said mammal a therapeutically effective amount of N-(3-ethynylphenyl)-6,7-bis(2-methoxyethoxy)-4-quinazolinamine mesylate in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

Patients that can be treated with N-(3-ethynylphenyl)-6,7-bis(2-methoxyethoxy)-4-quinazolinamine mesylate according to the methods of this invention include, for example, patients that have been diagnosed as having psoriasis, BPH, lung cancer, bone cancer, pancreatic cancer, skin cancer, cancer of the head and neck, cutaneous or intraocular melanoma, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphonas, cancer of the bladder, cancer of the kidney or ureter (e.g., renal cell carcinoma, carcinoma of the renal pelvis), or neoplasms of the central nervous system (e.g., primary CNS lymphona, spinal axis tumors, brain stem gliomas or pituitary adenomas).

DETAILED DESCRIPTION OF THE INVENTION

N-(3-ethynylphenyl)-6,7-bis(2-methoxyethoxy)-4-quinazolinamine mesylate has been found to exist in three distinct anhydrous polymorphic forms A, B and C and also as a monohydrate. The relationship of these forms is illustrated in the Scheme below.

N-(3-ethynylphenyl)-6,7-bis(2-methoxyethoxy)-4-quinazolinamine hydrochloride in dichloromethane and water, separating the organic phase, mixing isopropanol in the organic phase, adding methanesulfonic acid to the organic phase and then adding seed crystals of the mesylate anhydrate polymorph B to effect crystallization of polymorph B.

The anhydrous mesylate characterized as polymorph C may be prepared by mixing polymorph B, prepared as described above, in isopropanol at a temperature of about 60–70° C. for a period ranging from 18 hours to about 3 days. The anhydrous mesylate characterized as polymorph C

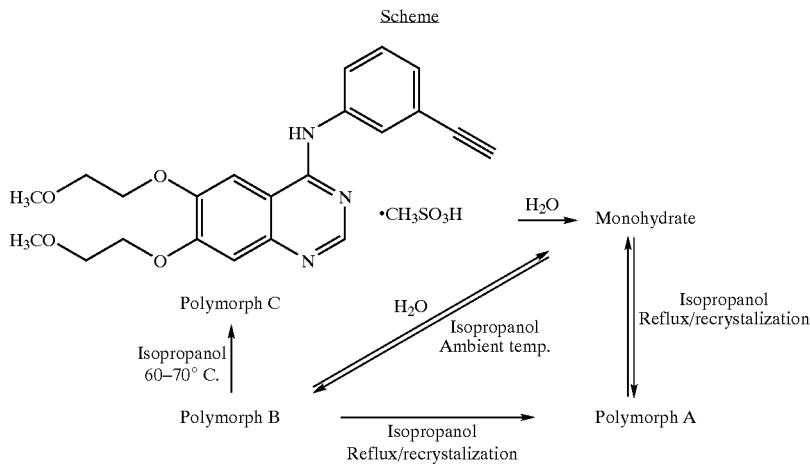

Scheme

N-(3-ethynylphenyl)-6,7-bis(2-methoxyethoxy)-4-quinazolinamine hydrochloride may be prepared as described in U.S. Pat. No. 5,747,498, issued May 5, 1998, referred to above. N-(3-ethynylphenyl)-6,7-bis(2-methoxyethoxy)-4-quinazolinamine mesylate monohydrate may be prepared by mixing N-(3-ethynylphenyl)-6,7-bis(2-methoxyethoxy)-4-quinazolinamine hydrochloride in ethyl acetate and water, warming the mixture to a temperature of about 60–70° C., adding sodium hydroxide to adjust the pH to within a range of about 10–11, separating the organic ethyl acetate phase, and then adding methanesulfonic acid to the organic phase to provide the mesylate monohydrate.

The anhydrous mesylate characterized as polymorph A may be prepared by mixing the mesylate monohydrate, prepared as described above, in ethyl acetate or isopropanol, heating the mixture to reflux for about 1 day, and then cooling to ambient temperature to allow crystallization.

The anhydrous mesylate characterized as polymorph B may be prepared by mixing the mesylate monohydrate in isopropanol and heating the mixture to about 45–55° C. for a period of about 5 hours. The anhydrous mesylate characterized as polymorph B may also be prepared by mixing may also be prepared by mixing N-(3-ethynylphenyl)-6,7-bis(2-methoxyethoxy)-4-quinazolinamine hydrochloride in ethyl acetate and water, treating the mixture with sodium hydroxide to raise the pH to about 8–9, separating the organic phase, mixing isopropanol in the organic phase, adding methanesulfonic acid to the organic phase, heating the mixture to about 70° C. for about 16 hours, and then cooling the mixture to effect crystallization of polymorph C.

Polymorphs A, B and C can be converted into the monohydrate by treatment with water. Each of the mesylate compounds of the present invention is more soluble in aqueous compositions than N-(3-ethynylphenyl)-6,7-bis(2-methoxyethoxy)-4-quinazolinamine hydrochloride, referred to above. Polymorph C is essentially non-hygroscopic and has resistance to thermal degradation.

The polymorphs A, B and C are characterized by the principal peaks found in the X-ray powder diffraction patterns shown below.

| Characteristic Peaks found in X-ray diffraction pattern of Polymorph A (*strongly absorbing peaks) | | | | | | | | | | |
|---|---|---|---|---|---|---|---|---|---|---|
| Peak No. | 1* | 2* | 3 | 4 | 5 | 6 | 7 | 8 | 9 | 10 |
| 2 q (°) Cu | 6.3 | 7.15 | 9.8 | 13.4 | 13.7 | 18.05 | 18.9 | 19.6 | 20.0 | 21.35 |
| d space | 14.1 | 12.3 | 9.0 | 6.6 | 6.4 | 4.9 | 4.7 | 4.5 | 4.4 | 4.15 |
| Peak No. | 11 | 12 | 13 | 14 | 15 | 16 | 17 | 18 | 19 | 20 |

-continued

| | | | |
|---|---|---|---|
| 2 q (°) Cu | 21.8 | 23.1 | 26.8 |
| d space | 4.1 | 3.85 | 3.3 |

Characteristic Peaks found in X-ray diffraction pattern of Polymorph B
(*strongly absorbing peaks)

| Peak No. | 1* | 2* | 3* | 4* | 5 | 6 | 7 | 8 | 9 | 10 |
|---|---|---|---|---|---|---|---|---|---|---|
| 2 q (°) Cu | 5.4 | 8.8 | 13.4 | 13.7 | 15.3 | 15.7 | 17.4 | 17.8 | 18.4 | 18.8 |
| d space | 16.3 | 10.1 | 6.6 | 6.5 | 5.8 | 5.65 | 5.1 | 5.0 | 4.8 | 4.7 |

| Peak No. | 11 | 12 | 13 | 14 | 15 | 16 | 17 | 18 | 19 | 20 |
|---|---|---|---|---|---|---|---|---|---|---|
| 2 q (°) Cu | 19.5 | 19.85 | 20.1 | 21.1 | 21.8 | 22.6 | 24.1 | 25.2 | 25.9 | 26.7 |
| d space | 4.55 | 4.5 | 4.4 | 4.2 | 4.1 | 3.9 | 3.7 | 3.5 | 3.4 | 3.3 |

| Peak No. | 21 | 22 | 23 | 24 | 25 | 26 | 27 | 28 | 29 | 30 |
|---|---|---|---|---|---|---|---|---|---|---|
| 2 q (°) Cu | 28.3 | 30.9 | | | | | | | | |
| d space | 3.1 | 2.9 | | | | | | | | |

Characteristic Peaks found in X-ray diffraction pattern of Polymorph C
(*strongly absorbing peaks)

| Peak No. | 1 | 2 | 3 | 4* | 5 | 6* | 7 | 8 | 9* | 10 |
|---|---|---|---|---|---|---|---|---|---|---|
| 2 q (°) Cu | 6.0 | 8.3 | 10.3 | 11.5 | 12.55 | 13.45 | 16.0 | 16.75 | 17.4 | 17.9 |
| d space | 14.7 | 10.6 | 8.6 | 7.7 | 7.05 | 6.6 | 5.5 | 5.3 | 5.1 | 4.95 |

| Peak No. | 11 | 12 | 13 | 14* | 15 | 16* | 17 | 18 | 19* | 20 |
|---|---|---|---|---|---|---|---|---|---|---|
| 2 q (°) Cu | 18.1 | 18.65 | 19.35 | 20.6 | 23.0 | 24.0 | 24.8 | 26.75 | 27.2 | 36.3 |
| d space | 4.9 | 4.75 | 4.6 | 4.3 | 3.9 | 3.7 | 3.6 | 3.3 | 3.3 | 2.5 |

Characteristic Peaks found in X-ray diffraction pattern of Monohydrate
(*strongly absorbing peak)

| Peak No. | 1* | 2 | 3 | 4 | 5 |
|---|---|---|---|---|---|
| 2 q (°) Cu | 5.7 | 7.0 | 11.3 | 20.5 | 25.1 |
| d space | 15.5 | 12.5 | 7.8 | 4.3 | 3.5 |

The compounds of the present invention are potent inhibitors of the erbB family of oncogenic and protooncogenic protein tyrosine kinases such as epidermal growth factor receptor (EGFR), erbB2, HER3, or HER4 and thus are all adapted to therapeutic use as antiproliferative agents (e.g., anticancer) in mammals, particularly in humans. The compounds of the present invention are also inhibitors of angiogenesis and/or vasculogenesis. In particular, the compounds of the present invention are useful in the prevention and treatment of a variety of human hyperproliferative disorders such as malignant and benign tumors of the liver, kidney, bladder, breast, gastric, ovarian, colorectal, prostate, pancreatic, lung, vulval, thyroid, hepatic carcinomas, sarcomas, glioblastomas, head and neck, and other hyperplastic conditions such as benign hyperplasia of the skin (e.g., psoriasis) and benign hyperplasia of the prostate (e.g., BPH). It is expected that a compound of the present invention may possess activity against a range of leukemias and lymphoid malignancies.

The compounds of the present invention may also be useful in the treatment of additional disorders in which aberrant expression ligand/receptor interactions or activation or signalling events related to various protein tyrosine kinases are involved. Such disorders may include those of neuronal, glial, astrocytal, hypothalamic, glandular, macrophagal, epithelial, stromal, or blastocoelic nature in which aberrant function, expression, activation or signalling of the erbB tyrosine kinases are involved. In addition, the compounds of the present invention may have therapeutic utility in inflammatory, angiogenic and immunologic disorders involving both identified and as yet unidentified tyrosine kinases that are inhibited by the compounds of the present invention.

The in vitro activity of the compounds of the present invention in inhibiting the receptor tyrosine kinase (and thus subsequent proliferative response, e.g., cancer) may be determined by the following procedure.

The activity of the compounds of the present invention, in vitro, can be determined by the amount of inhibition of the phosphorylabon of an exogenous substrate (e.g., $Lys_3$—Gastrin or polyGluTyr (4:1) random copolymer (I. Posner et al., J. Biol. Chem. 267 (29), 20638–47 (1992)) on tyrosine by epidermal growth factor receptor kinase by a test compound relative to a control. Affinity purified, soluble human EGF receptor (96 ng) is obtained according to the procedure in G. N. Gill, W. Weber, Methods in Enzymology 146, 82–88 (1987) from A431 cells (American Type Culture Collection, Rockville, Md.) and preincubated in a microfuge tube with EGF (2 μg/ml) in phosphorylabon buffer+vanadate (PBV: 50 mM HEPES, pH 7.4; 125 mM NaCl; 24 mM $MgCl_2$; 100 μM sodium orthovanadate), in a total volume of 10 μl, for 20–30 minutes at room temperature. The test compound, dissolved in dimethylsulfoxide (DMSO), is diluted in PBV, and 10 μl is mixed with the EGF receptor/EGF mix, and incubated for 10–30 minutes at 30° C. The phosphorylabon reaction is initiated by addition of 20 μl $^{33}$P-ATP/substrate mix (120 μM $Lys_3$-Gastrin (sequence in single letter code for amino acids, KKKGPWLEEEEEAYGWLDF), 50 mM Hepes pH 7.4, 40 μM ATP, 2 μCi γ-[$^{33}$P]-ATP) to the EGFr/EGF mix and incubated for 20 minutes at room temperature. The reaction is stopped by addition of 10 μl stop solution (0.5 M EDTA, pH 8; 2 mM ATP) and 6 μl 2N HCl. The tubes are centrifuged at 14,000 RPM, 4° C., for 10 minutes. 35 μl of supernatant from each tube is pipetted onto a 2.5 cm circle of Whatman P81 paper, bulk washed four times in 5% acetic acid, 1 liter per wash, and then air dried. This results in the binding of substrate to the paper with loss of free ATP on washing. The [$^{33}$P] incorporated is measured by liquid scintillation counting. Incorporation in the absence of substrate (e.g., lys$_3$-gastrin) is subtracted from all values as a background and percent inhibition is calculated relative to controls without test compound present. Such assays, carried out with a range of doses of test compounds, allow the determination of an approximate IC$_{50}$ value for the in vitro inhibition of EGFR kinase activity.

Other methods for determining the activity of the compounds of the present invention are described in U.S. Pat. No. 5,747,498, referred to above.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration. Parenteral administration is preferred.

The amount of the active compound administered will be dependent on the subject being treated, the severity of the disorder or condition, the rate of administration and the judgement of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumour substances, for example those selected from, for example, mitotic inhibitors, for example vinblastne; alkylating agents, for example cis-platin, carboplabn and cyclophosphamide; antimetabolites, for example 5-fluorouracil, cytosine; arabinoside and hydroxyurea, or, for example, one of the preferred anti-metabolites disclosed in European Patent Application No. 239362 such as N-(5[N-(3,4dihydro-2-methyl-4-oxoquinazolic-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and ant-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequenbal or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Addiionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

The examples and preparations provided below further illustrate and exemplify the compounds of the present invention and methods of preparing such compounds. It is to be understood that the scope of the present invention is not limited in any way by the scope of the following examples and preparations.

EXAMPLE 1

Preparation of N-(3-Ethynylphenyl)-6,7-bis(2-methoxyethoxy)-4-quinazolinamine Mesylate Salt Monohydrate The hydrochloride salt of N-(3-ethynylphenyl)-6,7-bis(2-methoxyethoxy)-4-quinazolinamine (12.0 g, 27.91 mmol), ethyl acetate (200 mL) and water (50 mL) were mixed together using mechanical agitation and then warmed to 60–70° C. The stirred mixture was treated portionwise with 50% aqueous sodium hydroxide (~14 mL) so that the pH of the aqueous phase was in the range 10–11. The mixture was allowed to settle and separate into two clear liquid phases. The aqueous phase was removed and the residual clear organic layer was heated to reflux in a Dean and Stark apparatus to azeotropically remove residual water. The volume of the organic layer was reduced by about 60 mL during this procedure. The hot organic solution was stirred and treated slowly with methanesulfonic acid (2.2 mL, 33.49 mmol) to give a hazy solution which on cooling to room temperature gave a crystal slurry. The crystal slurry was granulated for 1 hour in the temperature range 0–5° C., the crystals were isolated by filtration, washed with cold ethyl acetate (2×50 mL) and dried under vacuum at 35° C. to give the monohydrate 14.2 g, yield 100%, as a white crystalline solid mp 96–100° C.

The monohydrate is characterized by the powder X-ray diffraction pattern noted above.

EXAMPLE 2

Preparation of N-(3-ethynylphenyl)-6,7-bis(2-methoxyethoxy)-4-quinazolinamine Mesylate Salt Polymorph A A mixture of the monohydrate product of example 1 above, (15.0 g) and ethyl acetate (150 mL) was boiled at reflux in a Dean and Stark apparatus so that water was azeotropically removed over a period of 25 hours. The heat source was removed and the crystal slurry allowed to cool to room temperature and was granulated for 24 hours. The crystalline product was isolated by filtration and dried under vacuum at 38° C. to give polymorph A, 14.04 g, yield 97%, as a pale yellow crystalline solid mp 161–162° C.

Polymorph A is characterized by the powder X-ray diffraction pattern noted above.

EXAMPLE 3

Preparation of N-(3-ethynyphenyl)-6,7-bis(2-methoxyethoxy)-4-quinazolinamine Mesylate Salt Polymorph A A mixture of the monohydrate product of example 1 above, (20.0 g) and isopropanol (120 mL) was boiled at reflux for a period of 2 hours. The heat source was removed and the crystal slurry allowed to cool to room temperature and was granulated for 1 hour. The crystalline product was isolated by filtration and dried under vacuum at 38° C. to give polymorph A, 18.07 g, yield 93%, as a pale yellow crystalline solid mp 160–161° C.

Polymorph A is characterized by the powder X-ray diffraction pattern noted above.

EXAMPLE 4

Preparation of N-(3-ethynylphenyl)-6,7-bis(2-methoxyethoxy)-4-quinazolinamine Mesylate Salt Polymorph B A mixture of the monohydrate product of example 1 above, (10.0 g) and isopropanol (100 mL) was stirred mechanically in the temperature range 45–55° C. for a period of 5 hours. The heat source was removed and while the crystalline slurry was still above ambient temperature the crystalline product was isolated by filtration and dried under vacuum at 47° C. to give polymorph B, 9.06 g, yield 94%, as a white crystalline solid mp 142–144° C.

Polymorph B is characterized by the powder X-ray diffraction pattern noted above.

EXAMPLE 5

Preparation of N-(3-ethynylphenyl)-6,7-bis(2-methoxyethoxy)-4-quinazolinamine Mesylate Salt Polymorph B The hydrochloride salt of N-(3-ethynylphenyl)-6,7-bis(2-methoxyethoxy)-4-quinazolinamine (30.0 g, 69.79 mmol), dichloromethane (1125 mL) and water (300 mL) were mixed together using mechanical agitation and then treated with saturated sodium bicarbonate solution (300 mL). The mixture was allowed to settle and separate into two cloudy liquid phases. The aqueous phase was removed and further extracted with dichloromethane (300 mL) The organic layers were combined and washed with saturated sodium bicarbonate solution (300 mL), separated and dried by treatment with dried magnesium sulfate (50 g) and then filtered to give a clear organic layer which was concentrated by evaporation to a volume of about 300 mL. The resultant solution was treated with isopropanol (450 mL) and concentrated by evaporation to 300 mL giving a slurry mixture. The slurry mixture was treated slowly with methanesulfonic acid (4.5 mL, 69.79 mmol) to give a pale yellow solution which on cooling to room temperature gave a gum. Addition of seed crystals of polymorph B as prepared in example 4 eventually resulted in formation of a crystal slurry. The crystal slurry was granulated for 24 hours at ambient temperature overnight, the crystals were isolated by filtration, washed with isopropanol (50 mL) and dried under vacuum at 45° C. to give polymorph B, 23.43 g, yield 69%, as a white crystalline solid mp 142–144° C.

Polymorph B is characterized by the powder X-ray diffraction pattern noted above.

EXAMPLE 6

Preparation of N-(3-ethvnylphenyl)-6,7-bis(2-methoxyethoxy)-4-guinazolinamine Mesylate Salt Polymorph C A mixture of the polymorph B product of example 4 or 5 above, (10.0 g) and isopropanol (100 mL) was stirred mechanically in the temperature range 60–63° C. for a period of 3 days. The heat source was removed and the crystalline product was isolated by filtration and dried under vacuum at 47° C. to give polymorph C, 8.08 g, yield 81%, as a white crystalline solid mp 152–154° C.

Polymorph C is characterized by the powder X-ray diffraction pattern noted above.

EXAMPLE 7

Preparation of N-(3-ethynylphenyl)-6,7-bis(2-methoxyethoxy)-4-quinazolinamine Mesylate Salt Polymorph C A mixture of the polymorph B product of example 4 or 5 above, (20.0 g) and isopropanol (300 mL) was stirred mechanically in the temperature range 65–70° C. for a period of 22 hours. The conversion time varies, typically being in the range 18–24 hours for the conditions indicated. The conversion of polymorph B into polymorph C may be monitored using near-infrared spectroscopy after the method of Norris, Aldridge and Sekulic, *Analyst*, 1997, 122, 549. In this way a precise conversion time can be determined for each individual run. The heat source was removed and the mixture cooled to room temperature and granulated for a period of 1 hour. The crystalline product was isolated by filtration and dried under vacuum at 36° C. to give polymorph C, 19.42 g, yield 97%, as a white crystalline solid mp 153–155° C.

Polymorph C is characterized by the powder X-ray diffraction paftem noted above.

EXAMPLE 8

Preparation of N-(3-ethynylphenyl)-6,7-bis(2-methoxyethoxy)-4-guinazolinamine Mesylate Salt Polymorph C The hydrochloride salt of N-(3-ethynylphenyl)-6,7bis(2-methoxyethoxy)-4-quinazolinamine (100.0 g, 0.223 mole), ethyl acetate (2000 mL) and water (500 mL) were mixed together using mechanical agitation and thenwarmed to 40–45° C. The stirred mixture was treated portionwise with 50% aqueous sodium hydroxide (40 mL) so that the pH of the aqueous phase was in the range 8–9. The mixture was allowed to settle and separate into two clear liquid phases. The aqueous phase was removed and organic phase washed with water (300 mL). The resultant pale yellow organic solution was filtered to obtain a clear solution which was concentrated by distillation at atmospheric pressure to remove 1L of solvent. Isopropanol (2L) was added to the concentrate and a further 1L of solvents were removed by distillation at atmospheric pressure. The resultant concentrate was cooled to 40° C. and treated with methanesulfonic acid (15.1 mL, 0.233 mole) and allowed to crystallize. The crystal slurry was warmed to 62° C. for 18 hours. Monitoring with near-infrared spectroscopy after the method of Norris, Aldridge and Sekulic, *Analyst*, 1997 ,122, 549, indicated that no conversion to polymorph C had occurred. The temperature was raised to 70° C., after a period of 16 hours, near-infrared monitoring as described indicated the conversion was complete. The heat source was removed and the mixture cooled to 0–5° C. and granulated for a period of 1 hour. The crystalline product was isolated by filtration, washed with isopropanol (50 mL) and dried under vacuum at 33° C. to give polymorph C, 105.63 g, yield 93%, as a white crystalline solid mp 153–156° C.

Polymorph C is characterized by the powder X-ray diffraction pattern noted above.

What is claimed is:

1. A compound selected from the anhydrous and hydrate forms of N-(3-ethynylphenyl)-6,7-bis(2-methoxyethoxy)-4luinazolinamine mesylate.

2. A compound according to claim 1 wherein said compound is an anhydrous form of N-(3-ethynylphenyl)-6,7-bis(2-methoxyethoxy)-4uinazolinamine mesylate.

3. A compound according to claim 2 wherein said compound is polymorph A characterized by the following peaks in its X-ray powder diffraction pattern

| Peak No. | 1 | 2 | 3 | 4 | 5 | 6 | 7 | 8 | 9 | 10 |
|---|---|---|---|---|---|---|---|---|---|---|
| 2 q (°) Cu | 6.3 | 7.15 | 9.8 | 13.4 | 13.7 | 18.05 | 18.9 | 19.6 | 20.0 | 21.35 |
| d space | 14.1 | 12.3 | 9.0 | 6.6 | 6.4 | 4.9 | 4.7 | 4.5 | 4.4 | 4.15 |
| Peak No. | 11 | 12 | 13 | 14 | 15 | 16 | 17 | 18 | 19 | 20 |
| 2 q (°) Cu | 21.8 | 23.1 | 26.8 | | | | | | | |
| d space | 4.1 | 3.85 | 3.3 | | | | | | | |

4. A compound according to claim 2 wherein said compound is polymorph B characterized by the following peaks in its X-ray powder diffraction pattern

| Peak No. | 1 | 2 | 3 | 4 | 5 | 6 | 7 | 8 | 9 | 10 |
|---|---|---|---|---|---|---|---|---|---|---|
| 2 q (°) Cu | 5.4 | 8.8 | 13.4 | 13.7 | 15.3 | 15.7 | 17.4 | 17.8 | 18.4 | 18.8 |
| d space | 16.3 | 10.1 | 6.6 | 6.5 | 5.8 | 5.65 | 5.1 | 5.0 | 4.8 | 4.7 |
| Peak No. | 11 | 12 | 13 | 14 | 15 | 16 | 17 | 18 | 19 | 20 |
| 2 q (°) Cu | 19.5 | 19.85 | 20.1 | 21.1 | 21.8 | 22.6 | 24.1 | 25.2 | 25.9 | 26.7 |
| d space | 4.55 | 4.5 | 4.4 | 4.2 | 4.1 | 3.9 | 3.7 | 3.5 | 3.4 | 3.3 |
| Peak No. | 21 | 22 | 23 | 24 | 25 | 26 | 27 | 28 | 29 | 30 |
| 2 q (°) Cu | 28.3 | 30.9 | | | | | | | | |
| d space | 3.1 | 2.9 | | | | | | | | |

5. A compound according to claim 2 wherein said compound is polymorph C characterized by the following peaks in its X-ray powder diffraction pattern

| Peak No. | 1 | 2 | 3 | 4 | 5 | 6 | 7 | 8 | 9 | 10 |
|---|---|---|---|---|---|---|---|---|---|---|
| 2 q (°) Cu | 6.0 | 8.3 | 10.3 | 11.5 | 12.55 | 13.45 | 16.0 | 16.75 | 17.4 | 17.9 |
| d space | 14.7 | 10.6 | 8.6 | 7.7 | 7.05 | 6.6 | 5.5 | 5.3 | 5.1 | 4.95 |
| Peak No. | 11 | 12 | 13 | 14 | 15 | 16 | 17 | 18 | 19 | 20 |
| 2 q (°) Cu | 18.1 | 18.65 | 19.35 | 20.6 | 23.0 | 24.0 | 24.8 | 26.75 | 27.2 | 36.3 |
| d space | 4.9 | 4.75 | 4.6 | 4.3 | 3.9 | 3.7 | 3.6 | 3.3 | 3.3 | 2.5 |

6. A compound according to claim 1 wherein said compound is N-(3-ethynylphenyl)-6,7-bis(2-methoxyethoxy)-4-quirnazolinamine mesylate monohydrate.

7. A pharmaceutical composition for the treatment of a hyperproliferative disorder in a mammal which comprises a therapeutically effective amount of a compound according to claim 1 and a pharmaceutically acceptable carrier wherein the hyperproliferative disorder is brain cancer, lung cancer, squamous cell cancer, bladder cancer, gastric cancer, pancreatic cancer, breast cancer, head cancer, neck cancer, renal cancer, kidney cancer, ovarian cancer, prostate cancer, colorectal cancer, oesophageal cancer, gynecological cancer or thyroid cancer.

8. A method of treating a hyperproliferative disorder by inhibiting the epidermal growth factor receptor ("EGFR") in a mammal which comprises administering to said mammal a therapeutically effective amount of a compound according to claim 1 wherein the hyperproliferative disorder treatable by inhibition of the epidermal growth factor receptor ("EGFR") is brain cancer, squamous cell cancer, bladder cancer, gastric cancer, pancreatic cancer, breast cancer, head cancer, neck cancer, oesophageal cancer, prostate cancer, colorectal cancer, lung cancer, renal cancer, kidney cancer, ovarian cancer, gynecological cancer or thyroid cancer.

9. A pharmaceutical composition comprising the compound of claim 1 and a pharmaceutically acceptable carrier.

10. The pharmaceutical composition of claim 9, wherein the compound is essentially polymorph A.

11. The pharmaceutical composition of claim 9, wherein the compound is essentially polymorph B.

12. The pharmaceutical composition of claim 9, wherein the compound is essentially polymorph C.

* * * * *